(12) United States Patent
Rao et al.

(10) Patent No.: US 6,997,039 B2
(45) Date of Patent: Feb. 14, 2006

(54) CARBON NANOTUBE BASED RESONANT-CIRCUIT SENSOR

(75) Inventors: Apparao M. Rao, Anderson, SC (US); Saurabh Chopra, Raleigh, NC (US)

(73) Assignee: Clemson University, Clemson, SC (US)

( * ) Notice: Subject to any disclaimer, the term of this patent is extended or adjusted under 35 U.S.C. 154(b) by 0 days.

(21) Appl. No.: 10/785,421

(22) Filed: Feb. 24, 2004

(65) Prior Publication Data

US 2005/0183492 A1 Aug. 25, 2005

(51) Int. Cl.
  G01N 29/02 (2006.01)
  G01N 19/00 (2006.01)
  G01N 25/00 (2006.01)
  G01N 27/00 (2006.01)
  G01N 33/497 (2006.01)

(52) U.S. Cl. ................ 73/24.06; 73/24.01; 73/23.2
(58) Field of Classification Search ............... 73/24.06, 73/23.2, 23.34, 571, 579, 649, 24.01; 324/633, 324/652; 340/572.3, 572.5
See application file for complete search history.

(56) References Cited

U.S. PATENT DOCUMENTS

| | | | |
|---|---|---|---|
| 5,142,270 A | 8/1992 | Appalucci et al. | 340/572.3 |
| 5,182,544 A | 1/1993 | Aquilera et al. | 340/572.5 |
| 5,241,299 A | 8/1993 | Appalucci et al. | 340/572.3 |
| 5,514,337 A * | 5/1996 | Groger et al. | 422/82.08 |
| 5,754,110 A | 5/1998 | Appalucci et al. | 340/572.5 |
| 5,824,470 A | 10/1998 | Baldeschwieler et al. | 435/6 |
| 5,841,350 A | 11/1998 | Appalucci et al. | 340/572.3 |
| 5,861,809 A | 1/1999 | Eckstein et al. | 340/572.3 |
| 6,231,744 B1 | 5/2001 | Ying et al. | 205/324 |
| 6,287,765 B1 | 9/2001 | Cubicciotti | 435/6 |
| 6,297,063 B1 | 10/2001 | Brown et al. | 438/2 |
| 6,359,288 B1 | 3/2002 | Ying et al. | 257/14 |
| 6,359,444 B1 | 3/2002 | Grimes | 324/633 |
| 6,400,271 B1 | 6/2002 | Davies, Jr. et al. | 340/572.1 |
| 6,555,945 B1 | 4/2003 | Baughman et al. | 310/300 |
| 6,598,459 B1 | 7/2003 | Fu | 73/23.34 |
| 6,605,266 B1 | 8/2003 | Nesper et al. | |
| 2002/0034757 A1 | 3/2002 | Cubicciotti | |
| 2002/0153882 A1 | 10/2002 | Grimes et al. | |
| 2002/0182648 A1 | 12/2002 | Mojtabai | |
| 2003/0065206 A1 | 4/2003 | Bolskar et al. | |
| 2003/0096104 A1 | 5/2003 | Tobita et al. | |
| 2003/0144185 A1 | 7/2003 | McGimpsey | |

OTHER PUBLICATIONS

Article—*A Carbon Nanotube-based Sensor for $CO_2$ Monitoring*, Keat G. Ong and Craig A. Grimes, Sensors, vol. 1, 2001, pp. 193-205.

(Continued)

*Primary Examiner*—Hezron Williams
*Assistant Examiner*—Tamiko Bellamy
(74) *Attorney, Agent, or Firm*—Dority & Manning, P.A.

(57) ABSTRACT

Disclosed are resonant gas sensors and methods for forming and using the disclosed sensors. The sensors include a resonator including a layer comprising adsorptive nanostructures, for example carbon nanotubes, activated carbon fibers, or adsorptive nanowires. The dielectric of the resonator is in electrical communication with the layer comprising adsorptive nanostructures such that the effective resonant frequency of the resonator depends on both the dielectric constant of the dielectric as well as the dielectric constant of the adsorptive layer. In some embodiments, the nanostructures can be degassed. The sensors can detect the presence of polar gases, non-polar gases, organic vapors, and mixtures of materials with both high sensitivity and high selectivity.

30 Claims, 12 Drawing Sheets

OTHER PUBLICATIONS

Article—*A resonant printed-circuit sensor for remote query monitoring of envirommental parameters*, Keat Ghee Ong and Craig A. Grimes, Smart Mater. Struct., vol. 9, 2000, pp. 421-428.

Article—*A Wireless, Passive Carbon Nanotube-Based Gas Sensor*, Keat Ghee Ong, Kefeng Zeng, and Craig A. Grimes, IEEE Sensors Journal, vol. 2, No. 2, Apr. 2002, pp. 82-88.

Article—*Carbon-nanotube-based resonant-circuit sensor for ammonia*, S. Chopra, A Pham, J. Gaillard, A. Parker, and A. M. Rao, Applied Physics Letters, vol. 80, No. 24, Jun. 17, 2002, pp. 4632-4634.

Article-*Doped Carbon Nanotubes for Hydrogen Storage*, Ragaiy Zidan, 4 pages.

Article—*Electronic properties of $Gd@C_{82}$ metallofullerene peapods: $(Gd@C_{82})@SWNTs$*, T. Okazaki, T. Shimada, K. Suenaga, Y. Ohno, T. Mizutani, J. Lee, Y. Kuk, and H. Shinohara, Appl. Phys. A—Materials Science & Processing, vol. 76, 2003, pp. 475-478.

Article—*Gas sensing characteristics of multi-wall carbon nanotubes*, O.K. Varghese, P.D. Kichambre, D. Gong, K.G. Ong, E.C. Dickey, and C.A. Grimes, Sensors and Actuators B, vol. 81, 2002, pp. 32-41.

Article—*Hydrogen adsorption and cohesive energy of single-walled carbon nanotubes*, Y. Y, C. C. Ahn, C. Witham, B. Fultz, J. Liu, A. G. Rinzler, D. Colbert, K. A. Smith, and R. E. Smalley, Applied Physics Letters, vol. 74, No. 16, Apr. 19, 1999, pp. 2307-2309.

Article—*Hydrogen Storage in Single-Walled Carbon Nanotubes at Room Temperature*, C. Liu, Y. Y. Fan, M. Liu, H. T. Cong, H. M. Cheng, and M. S. Dresselhaus, Science, vol. 286, Nov. 5, 1999, pp. 1127-1129.

Article—*Nanotube Molecular Wires as Chemical Sensors*, Jing Kong, Nathan R. Franklin, Chongwu Zhou, Michael G. Chapline, Shu Peng, Kyeongjae Cho, and Hongjie Dai, Science, vol. 287, Jan. 28, 2000, pp. 622-625.

Article—*Ozonation of Single-Walled Carbon Nanotubes and Their Assemblies on Rigid Self-Assembled Monolayers*, Chem. Mater., vol. 14, 2002, pp. 4235-4241.

Article—*Raman Spectroscopic Investigation of $H_2$ HD, and $D_2$ Physisorption on Ropes of Singled-Walled, Carbon Nanotubes*, Keith A. Williams, Bhabendra K. Pradhan, Peter C. Eklund, Milen K. Kostov, and Milton W. Cole (arXiv: cond-mat/0104476 vl), Apr. 25, 2001, 6 pages.

Article—*Single-walled carbon nanotube—amylopectin complexes*, Leszek Stobinski, Piotr Tomasik, Cheng-Yi Lii, Hua-Han Chan, Hong-Ming Lin, Hsiang-Lin Liu, Chun-Tao Kao, Kun-Sheng Lu, Carbohydrate Polymers, vol. 51, 2003, pp. 311-316.

Article—*Water-vapor effect on the electrical conductivity of a single-walled carbon nanotube mat*, A. Zahab, L. Spina, P. Poncharal, and C. Marliere, Physical Review B, vol. 62, No. 15, Oct. 15, 2000-I, pp. 10 000-10 003.

Pages from nanotechweb.org entitled "Array of carbon nanotube devices detects gas molecules", Feb. 11, 2003, 2 pages.

Pages from nasatech.com entitled "Carbon Nanotubes as Resonatros for RF Spectrum Analyzers", Nasa's Jet Propulsion Laboratory, Pasadena, California, 2 pages.

Article—*Selective gas detection using a carbon nanotube sensor*, S. Chopra, K. McGuire, N. Gothard, and A. M. Rao, Applied Physics Letters, vol. 83, No. 11, Sep. 15, 2003, pp. 2280-2282.

Presentation Abstract—*Carbon Nanotubes Based Resonant Circuit Sensors For Gas Detection*, S. Chopra, K. McGuire, N. Gothard, A. Pham, and A. M. Rao, for the Mar. 2003 Meeting of The American Physical Society, 1 page.

\* cited by examiner

CARBON NANOTUBE BASED RESONANT-CIRCUIT SENSOR

FEDERALLY SPONSORED RESEARCH AND DEVELOPMENT

The United States Government may have rights in this invention pursuant to National Science Foundation Grant No. 0132573 and through the National Science Foundation NIRT DMI-0210559.

BACKGROUND OF THE INVENTION

Sensors are used in countless applications throughout a myriad of industries based upon their ability to respond in a measurable fashion to a stimulus. Sensors are used to measure or respond to everything from the presence of hazardous liquids or gases in a manufacturing process to the current weather conditions anywhere on the planet to stolen goods passing out the door of a retail establishment. With the advent of increasingly automated manufacturing processes as well as the possibility of hazardous environmental conditions caused by natural or induced disaster, gas sensors, such as may be utilized to discern the presence of gas or vapor-born pathogens, have attracted increasing attention of late.

In general, gas sensors are those sensors which convert a chemical signal to an electrical signal, with a change in the chemical input leading to a measurable change in the electrical output. Traditionally, gas sensors have been formed using semi-conducting oxides as the sensing material. These materials require expensive microfabrication techniques to form the sensors, however, and often only have the high sensitivities required to discern materials in low concentrations (such as parts per million) at high temperature (e.g., 200–600° C.).

Recently, carbon nanotubes have been examined as possible gas sensing materials due to their electrical and mechanical properties as well as their high specific surface area. For example, chemical sensors based on individual nanotubes have been reported by Kong, et al. ("Nanotube Molecular Wires as Chemical Sensors," *Science*, 287, 622 (2000)). These sensors utilize the measurable change in the electrical resistance of a nanotube upon exposure to gases like $NO_2$ and $NH_3$ to sense the presence of the gas.

Inductor-capacitor (LC) resonant sensors are a type of solid-state sensor based upon the permittivity of a material. LC resonant sensors have been widely utilized as remote anti-theft sensors. In these remote sensing systems, an RF transmitter/receiver sends a microwave signal at a targeted frequency through an interrogation zone. The presence in the interrogation zone of an activated tag including a dielectric material having the targeted resonant frequency can be detected by the receiver, which then sets off an alarm.

More recently, research has been carried out to expand the use of LC resonant sensors beyond these simple yes- or no-type applications. Specifically, LC resonant sensors have been combined with carbon nanotube materials for utilization as gas sensors. For example, Ong, et al. ("A Wireless, Passive Carbon Nanotube-Based Gas Sensor," IEEE Sensors Journal, Vol. 2, No. 2, April, 2002) has described a gas sensor formed of a responsive multi-wall carbon nanotube/silicon dioxide composite layer deposited on a planar LC resonant circuit. As the permittivity and/or conductivity of the $MWNT/SiO_2$ composite changes with adsorption of $CO_2$, $O_2$, or $NH_3$, so does the resonant frequency of the sensor, which can be remotely monitored through a loop antenna. The sensors showed reversible response to $O_2$ and $CO_2$, and an irreversible response to $NH_3$.

Chopra, et al. ("Carbon-nanotube-based Resonant-circuit Sensor for Ammonia," Applied Physics Letters, Volume 8, Number 24, 2002, which is incorporated herein in its entirety by reference thereto) have described an ammonia sensor formed of a simple micro-strip circular disk resonator coated with carbon nanotubes (either single-walled or multi-walled nanotubes) on the surface. The sensors show a shift in resonant frequency upon adsorption of ammonia of about 4.375 MHz for a single-walled nanotube (SWNT) sensor and a shift of about 3.25 MHz for a multi-walled nanotube (MWNT) sensor, and can detect the presence of ammonia down to a concentration of about 100 ppm.

Despite these advances in addressing the needs for improved gas sensors, there remains room for variation and improvement within the art.

SUMMARY OF THE INVENTION

The present invention is directed to resonant circuit gas sensors and methods of forming and utilizing the disclosed gas sensors. For instance, in one embodiment, the present invention is directed to a gas sensor including a resonator comprising a dielectric material and a layer including an amount of adsorptive nanostructures applied to a surface of the resonator, wherein this layer is in electrical communication with the dielectric material. That is, the electromagnetic field coupling characteristics of the resonator have been relaxed from that of a perfectly matched resonator such that electromagnetic field lines can couple to both the layer of the sensor that includes the adsorptive nanostructures as well as through the dielectric substrate. As such, the effective resonant frequency of the gas sensor can depend not only on the dielectric constant of the dielectric material, but also on the dielectric constant of the layer comprising the adsorptive nanostructures. In addition, the dielectric constant of this layer can vary in proportion to the dielectric of a material adsorbed onto or in electrical communication with the nanostructures. The adsorptive nanostructures can be, for example, carbon nanotubes, activated carbon fibers, or adsorptive nanowires.

In one embodiment of the invention, the adsorptive nanostructures can be degassed carbon nanotubes. In this embodiment, the carbon nanotubes can be degassed by a process including holding the resonator at low pressure and high temperature for a period of time following formation of the resonator. For example, the resonator can be held at a pressure between about $1\times10^{-5}$ and $2\times10^{-4}$ torr for a period of at least about 12 hours while simultaneously holding the resonator at a temperature of between about 100° C. and about 125° C.

The disclosed sensors can also include an analyzer for obtaining the resonant frequency of the resonator. Moreover, the analyzer can be either hard wired to the resonator or in remote communication with the resonator, such as via a radio frequency signal.

In one embodiment, the adsorptive nanostructures can be carbon nanotubes. In this embodiment, the carbon nanotubes can be either single-walled nanotubes (SWNTs) or multi-walled nanotubes (MWNTs), as desired. For example, in one embodiment, a layer of carbon nanotubes can be applied to a surface of the resonator and can include SWNT bundles. Individual SWNT bundles can have, in one embodiment, diameters between about 5 and about 200 nanometers. In another embodiment, the layer of nanotubes applied to a surface of the resonator can include MWNTs. In general, MWNTs can have diameters between about 5 and about 100 nanometers.

The depth of the layer comprising adsorptive nanostructures can vary. For example, in one embodiment, the layer of the sensor including the adsorptive nanostructures can be about 2 $\mu$m in depth.

In one particular embodiment, the resonator of the disclosed sensor can be a micro-strip circuit board resonator. In this embodiment, the resonator can include a ground plane, a dielectric substrate applied to the ground plane, a conducting micro-strip applied to the dielectric substrate, and a layer comprising adsorptive nanostructures, such as degassed carbon nanotubes, applied to a surface of the conducting micro-strip. In one particular embodiment, the conducting micro-strip can be a circular disk.

When utilizing the disclosed sensors, in one embodiment, the resonator of the sensor can be contacted with a gaseous stream. Material in the stream can adsorb to the adsorptive nanostructures on the resonator, which can cause a change in the effective dielectric constant of the resonator that can be reflected by a change in the resonant frequency of the resonator. Beneficially, the sensors can be utilized at room temperature to detect very low concentrations of materials.

In one embodiment, the disclosed sensor can be utilized to detect the presence of a vaporous organic material in a gaseous stream. In one particular embodiment, the organic material can be adsorbed onto a layer comprising adsorptive nanostructures including as-prepared carbon nanotubes, that is, in this embodiment, the nanostructures can be carbon nanotubes that have not been degassed prior to use.

In some embodiments of the present invention, the adsorptive nanostructures can be degassed prior to use. In this embodiment, the sensitivity and selectivity of the sensors can be such that the sensors can detect the presence of polar gases, non-polar gases, organic vapors, or mixtures of such at very low concentrations, for example down to about 100 ppb. For instance, in certain embodiments, the sensors can detect materials at concentrations between about 100 ppb and about 1500 ppm.

The disclosed sensors can have very fast response times, on the order of about 10 minutes. In addition, the sensors can, in some embodiments, have recovery times also on the order of about 10 minutes.

BRIEF DESCRIPTION OF THE DRAWINGS

A full and enabling disclosure of the present invention, including the best mode thereof, to one of ordinary skill in the art, is set forth more particularly in the remainder of the specification, including reference to the accompanying figures, in which.

Figure 1:
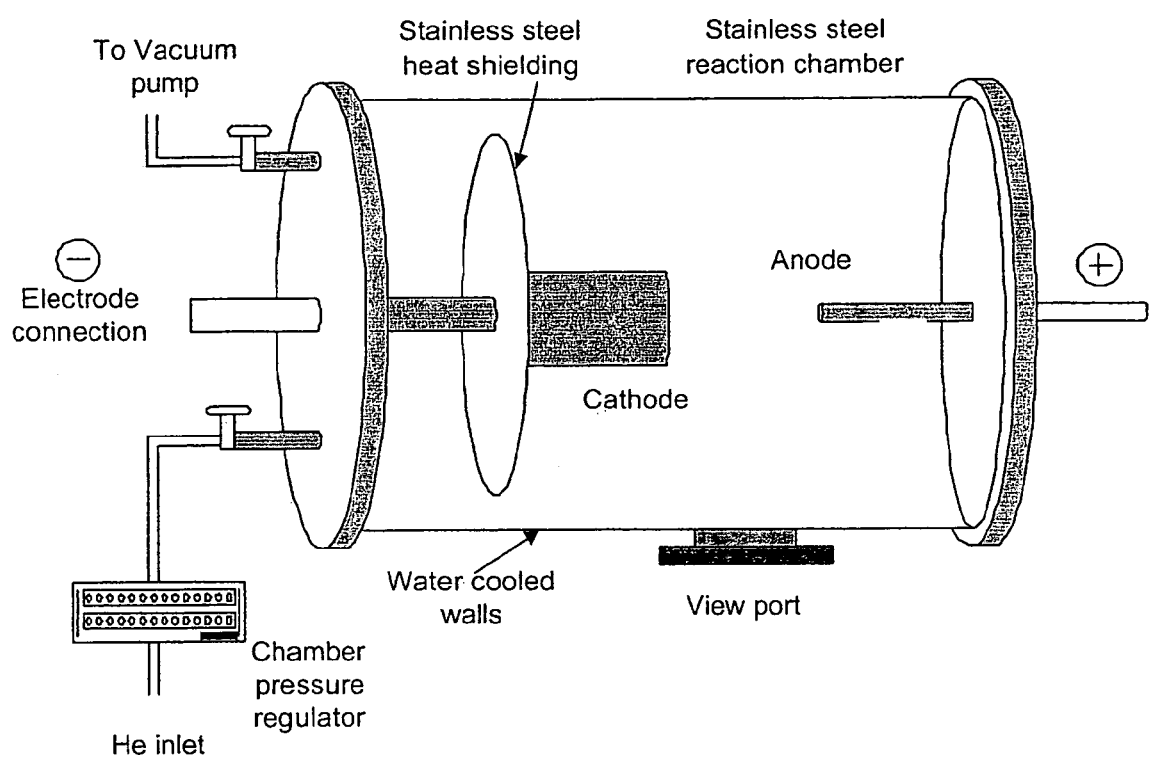
FIG. 1 is a schematic diagram of an electric arc discharge apparatus such as may be utilized in forming SWNTs of the present invention.

Repeat use of reference characters in the present specification and drawings is intended to represent the same or analogous features or elements of the present invention.

DETAILED DESCRIPTION OF THE INVENTION

Reference will now be made in detail to various embodiments of the invention, one or more examples of which are set forth below. Each embodiment is provided by way of explanation of the invention, not limitation of the invention. In fact, it will be apparent to those skilled in the art that various modifications and variations may be made in the present invention without departing from the scope or spirit of the invention. For instance, features illustrated or described as part of one embodiment, may be used in another embodiment to yield a still further embodiment. Thus, it is intended that the present invention cover such modifications and variations as come within the scope of the appended claims and their equivalents.

The present invention is generally directed to gas/vapor sensors that are able to detect the presence of a large number of different substances at very low concentration levels. The invention is also directed to methods for forming the disclosed sensors as well as methods for utilizing the disclosed sensors. More specifically, the presently disclosed sensors can detect the presence of both polar and non-polar gases. In addition, the disclosed sensors can detect the presence of organic vapors. Beneficially, the disclosed sensors display both high sensitivity, able in some embodiments to detect the presence of materials at concentrations on the order of 100 parts per billion (ppb), as well as high selectivity, showing measurably different responses to a wide variety of different materials. Moreover, the disclosed sensors can operate at room temperature and can have fast response and recovery times, on the order of about 10 minutes. In addition, in certain embodiments, the disclosed sensors can completely recover their original electrical state following the recovery procedure, with little or no residual effects on the sensor due to previous use. In one embodiment, the disclosed sensors can operate in remote sensing systems, in which the analyzer and the material sensing portion of the sensor are in remote contact, such as through an RF transmitter/receiver, for example. Alternatively, in other embodiments, the analyzer and sensing portions of the sensors can be in hard wired communication.

The basic principle of gas/vapor sensors is the conversion of a chemical signal (the presence of the gas or vapor) to an electrical signal. The presently disclosed sensors are microwave resonant-circuit-type sensors in which exposure to a gas or vapor can cause a change in the dielectric behavior of the sensor, which can be demonstrated by variation in the resonant frequency of the sensor.

In general, a microwave resonator can be thought of as a high frequency substitute of a lower frequency lumped circuit LC network as is generally known in the art. A conventional microwave resonator has a bounded electromagnetic field in a dielectric material that is encased by metallic walls. The electric and magnetic energies are stored in the electric and magnetic fields inside the dielectric and the corresponding lumped circuit equivalent inductances and capacitances can be calculated from the stored fields. Thus, the resonant frequency of any particular resonator will depend not only on the geometry of the resonator, but also on the effective dielectric constant of the dielectric materials. For example, when considering a circular disk resonator, the resonant frequency of the resonator can be approximated (by neglecting the edge fields of the disk) by the expression:

$$f = \frac{1.841 c}{2\pi a \sqrt{\varepsilon_r}}$$

where c is the velocity of light, $\varepsilon_r$ is the relative dielectric constant of the substrate, a is the radius of the circular disk and f is the resonant frequency of the resonator.

In the present invention, the resonator portion of the sensor can include several different materials, all of which can contribute to the electrical characteristics, and specifically to the effective dielectric constant, and hence the resonant frequency, of the sensor. In particular, the disclosed sensors include a layer including adsorptive nanostructures at a surface of the resonator. Suitable adsorptive nanostructures can be any structure formed on a nano-scale that can adsorb materials from a gaseous state, i.e., gases or vapors. Adsorptive nanostructures can include, for example, carbon nanotubes (either single-walled nanotubes (SWNTs) or multi-walled nanotubes (MWNTs)), activated carbon fibers, adsorptive nanowires, and the like. Moreover, when considering carbon nanotubes, both functionalized and non-functionalized carbon nanotubes are encompassed by the invention. In addition, nanotubes with either open ends or closed end-caps can be utilized with the disclosed invention.

The design of the resonators of the disclosed sensors are such that the electromagnetic field coupling characteristics of the resonator have been relaxed from that of a perfectly matched resonator. In this manner, electromagnetic field lines can pass through the area of the sensor in which the adsorptive nanostructure-containing layer is located as well as through the dielectric substrate itself. Thus, the dielectric material and the adsorptive nanostructure-containing layer are in electrical communication with one another, and the electrical characteristics of both the dielectric and the adsorptive nanostructure-containing layer can affect the electrical characteristics of the sensor, and specifically the resonant frequency of the sensor.

In the present invention, it is the ability of nanostructures to adsorb materials as well as the high specific surface area of the nanostructures which are of particular relevance. For instance, due to the high specific surface area of nanostructures, little nanostructure material is required on the sensors to provide ample sites for gas or vapor interaction, and the sensors of the present invention can, if desired, be quite small.

Carbon nanotubes in general can exhibit exceptional physical strength, elasticity, hydrogen storage capability, adsorption capability, high specific surface area, and resistance to most chemicals. As such, in one particular embodiment of the present invention, the adsorptive nanostructures of the disclosed invention can be carbon nanotubes. The following discussion is therefore directed to this particular embodiment. It should be made clear however, that though the following discussion is directed to one particular exemplary embodiment, any adsorptive nanostructures can equally be utilized in the disclosed invention, and in much of the following discussion, the term 'adsorptive nanostructure' is directly interchangeable with the term 'carbon nanotube'.

The ability of carbon nanotubes to quickly adsorb materials is of benefit to the disclosed sensors. More particularly, when considering the effective dielectric constant and associated resonant frequency of the resonators of the disclosed sensors, not only will the presence of the nanotubes on the resonator affect the resonant frequency, but the added presence of materials adsorbed onto the nanotubes will also affect the resonant frequency. In addition, as dielectric constant is an inherent characteristic of a material, the effective dielectric constant of the resonator, and hence the resonant frequency of the resonator, will vary depending on exactly what materials have been adsorbed onto the carbon nanotubes. Thus, a shift in resonant frequency of the resonator can be observed upon adsorption of a material to the nanotubes. Moreover, this shift will vary depending on what material is adsorbed. Beneficially, the ability of the carbon nanotube-containing layer to adsorb a material does not require the use of functionalized carbon nanotubes for enhanced selectivity to any particular chemical species, and as such, the formation processes for the disclosed sensors can be relatively simple and inexpensive.

In certain embodiments of the present invention, the disclosed sensors can be made more sensitive by degassing the adsorptive layer of the resonator. In this particular embodiment, it has been found that the sensitivity of the sensors can be improved, providing sensors that can respond to the presence of gases and vapors in concentration levels as little as about 100 ppb. In addition, when the nanotube-containing material is degassed prior to use the sensors can have measurable response to an increased number of materials. For example, when utilizing degassed nanotubes in the sensors, the sensors can indicate a measurable variation in resonant frequency of the resonator upon exposure to polar as well as non-polar gases.

Figure 4A:
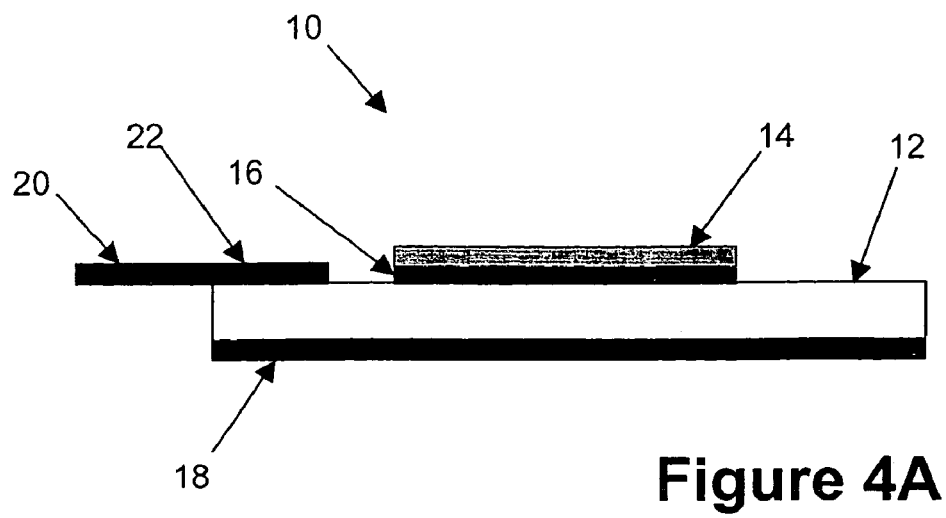
FIG. 4 illustrates one embodiment of a portion of a resonant-circuit sensor according to the present invention.
Figure 4B:
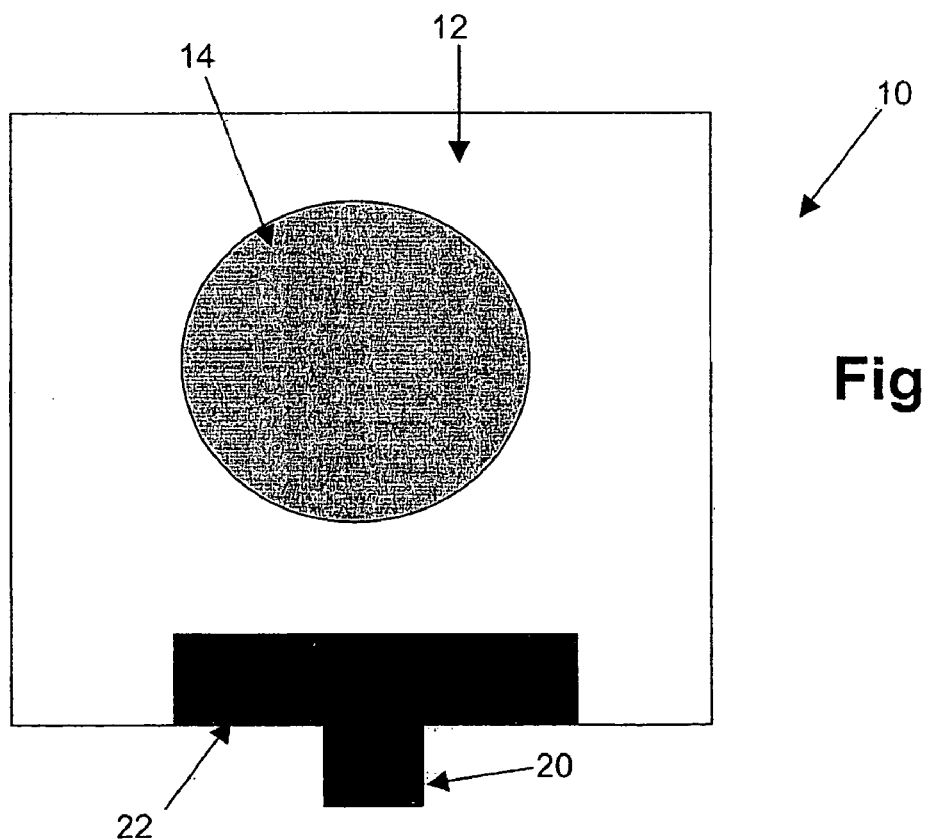

Referring to FIGS. 4A and 4B, one embodiment a resonator generally 10 that can be utilized in the disclosed sensors is illustrated. In this particular embodiment, the resonator 10 is a microwave circuit board resonator comprising a ground plane 18, a dielectric substrate 12 and a conducting micro-strip 16. In one embodiment, the ground plane 18 can be a metallic plate, such as a copper plate. A dielectric substrate 12 can be applied to the surface of the ground plane 18, as shown. The dielectric substrate 12 can be any suitable dielectric material as is known in the art. In one embodiment, the pre-shaped conducting micro-strip 16 can be applied to the surface of the dielectric substrate 12. In another embodiment, the conducting micro-strip 16 can be applied and then etched to the desired final geometry following application. In yet another embodiment, the resonator 10 can be formed from a Duroid board, i.e. a dielectric sandwiched between metal (usually copper) plates, in which the desired pattern for the micro-strip 16 has been formed and etched in the metal on one side of the board.

It should be understood that the specific circuit board materials, geometries, and production methods described for the microwave circuit board of this particular embodiment of the disclosed sensors are not critical to the presently disclosed invention, and other microwave circuit board materials and geometries as are generally known in the art may alternatively be utilized for any of the ground plane 18, the substrate 12, and/or the conducting micro-strip 16.

As can be seen, in the embodiment illustrated in FIGS. 4A and 4B, resonator 10 is a circular disk resonator, which is a type of micro-strip resonator as is generally known in the art.

There are several different types of resonators and resonator geometries known in the art, however, and, in particular, as the effective dielectric constant will vary with the geometry of the resonator, among other factors, other types of resonators are also encompassed by the disclosed invention. For example, in other embodiments of the invention, different geometries of micro-strip resonators are contemplated, as previously discussed. In addition, however, other types of resonators could be utilized in the disclosed sensors including, for example, rectangular cavity resonators or dielectric resonators. In general, any type of resonator can be utilized in the sensor as long as the resonator defines at least one surface to provide suitable interaction between the sensor and the gaseous materials to be detected. In addition, the dielectric of the resonator must be in electrical communication with adsorptive nanostructures located on this surface.

According to the present invention, the resonator includes a layer including an amount of adsorptive nanostructures, such as carbon nanotubes, on a surface. For example, in the embodiment illustrated in FIGS. 4A and 4B, a layer 14 including carbon nanotubes can be physically coated or directly deposited on a surface of the conducting micro-strip 16. As can be seen, the layer 14 containing carbon nanotubes need not be in physical contact with the dielectric material 12 of the resonator, but the coupling characteristics of the resonator can be relaxed from that of a perfectly matched resonator such that the layer 14 containing carbon nanotubes can be in electrical communication with the dielectric material 12. As such, the electrical characteristics of the nanotube layer, e.g., the dielectric constant, the conductivity, etc. can affect the electrical characteristics of the resonator 10. Similarly, material adsorbed to the carbon nanotubes can also affect the electrical characteristics of the resonator. Thus, upon adsorption of a material to the carbon nanotubes, a measurable change in the electrical characteristics of the resonator 10 can be observed.

Carbon nanotubes that can be used in the disclosed sensors can be either SWNTs or MWNTs, as desired. In addition, the nanotubes can be formed according to any formation process as is known in the art. For example, in one embodiment, the sensor can include a layer of SWNTs formed according to an electric arc method, one embodiment of which is illustrated in FIG. 1. According to this method, an electric arc can be generated in an inert atmosphere, for example, helium at about 600 torr, between a cathode and an anode. In general, the cathode can be a graphite rod and the anode can be a catalyst-impregnated graphite rod, such as those available from Carbolex, Inc. of Lexington, Ky. For example, the catalyst can be a mixture of 1 at. % Yttrium and 4.2 at. % Nickel. An arc discharge can be created by a current of about 100 A, creating a voltage of about 25 volts between the two electrodes. Typical synthesis times are of the order of two hours and result in a web-like material containing the SWNTs between the cathodes and the reactor walls. SWNTs produced according to this method can have a diameter of about 1.4 nm and are generally several microns in length. The electric arc method for formation of the SWNTs of the invention may be preferred in some embodiments due to high yields, up to about 70%.

Figure 2:
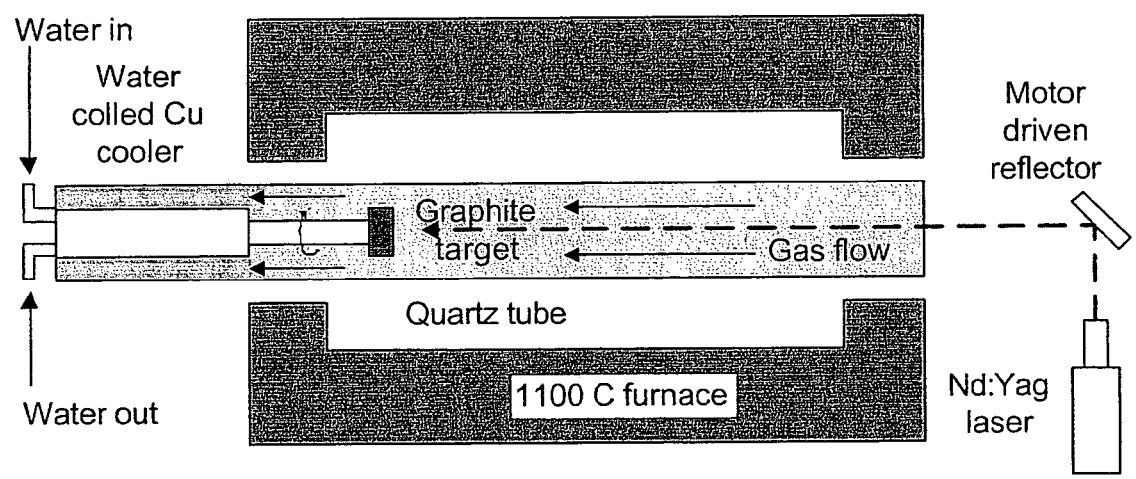
FIG. 2 is a schematic diagram of a laser-vaporization apparatus such as may be utilized in forming SWNTs of the present invention.

In another embodiment, SWNTs can be utilized in the invention formed according to the laser-vaporization method, an example of which is illustrated in FIG. 2. According to this method, a laser beam, controlled by a motor driven reflector, can be focused on a rotating target about one inch in diameter. The target is a metal/graphite composite and can be placed at the center of a furnace. The furnace can be maintained at a high temperature, about 1100° C., for example. The laser beam scans laterally across the target and the target is ablated uniformly as it rotates, as shown by the arrow in FIG. 2. The process is carried out in an inert atmosphere, and the material produced by the laser vaporization of the target is swept by inert flow out of the furnace and collected in a lower temperature zone, such as on a water-cooled condenser. In general, SWNTs produced according to the laser-vaporization method can be larger than those produced according to the electric-arc method.

Figure 3:
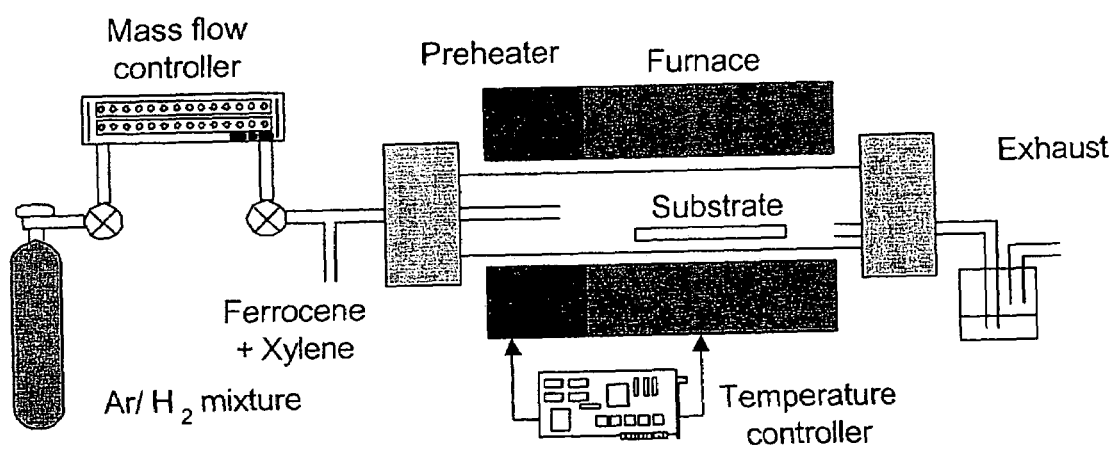
FIG. 3 is a schematic diagram of a CVD apparatus such as may be utilized in forming MWNTs of the present invention.

In certain embodiments of the present invention, the carbon nanotube-containing layer of the sensor can include multi-walled carbon nanotubes (MWNTs). In one embodiment, MWNTs can be formed according to a chemical vapor deposition method, such as that illustrated in FIG. 3. In the embodiment shown in FIG. 3, highly aligned and high purity MWNTs can be produced by the thermal decomposition of a xylene-ferrocene mixture. The xylene serves as the hydrocarbon source and ferrocene provides the iron catalyst nanoparticles that can seed the nanotubes that are grown. According to one process, ferrocene (approximately 6.5 at. %) can be dissolved in xylene and fed into a quartz tube at a flow rate of about 1 ml/hr. The mixture can vaporize upon reaching the end of the pre-heater (maintained at about 200° C.), and the vapors can then be carried into the furnace in an $Ar/H_2$ flow. The furnace is maintained at a temperature (e.g., about 750° C.) that enables the xylene/ferrocene mixture to decompose and form the MWNTs. The nanotubes are harvested from the walls of the furnace and, in one embodiment, can have a diameter of about 25 nm.

It should be understood that the specific method of forming the nanotubes of the disclosed sensors is not critical to the invention, and the described methods are merely exemplary, and not meant to be limiting in any way to the invention. In general, SWNT bundles utilized in the disclosed sensors can be between about 5 and about 200 nanometers in diameter, and MWNTs utilized in the disclosed sensors can be between about 5 and about 100 nanometers in diameter.

Referring again to FIG. 4, in this embodiment, following formation, the nanotube-containing material can be coated on the surface of the conducting micro-strip 16 to form a layer 14 on a surface of the resonator 10. For example, in one embodiment, the nanotubes can be coated on top of the conducting micro-strip 16 using conductive epoxy such as CW2400 available from Circuit Works of Lake Bluff, Ill. In another embodiment, the nanotube material can be directly deposited on the resonator. For instance, in one embodiment, the carbon nanotube-containing material can be directly deposited on the conducting micro-strip during the nanotube formation process such that the carbon nanotubes can be directly grown on the surface of the conducting micro-strip of the resonator.

The depth and purity of the nanotube-containing layer 14 on the sensors is not critical to the invention. In particular, all that is necessary is that suitable amounts of nanotube material be coated on the sensor so as to provide an amount of surface area for interaction with the materials to be detected. For example, in one embodiment, the disclosed sensor can include an adsorptive nanostructure-containing layer that is about 2 μm thick.

The sensors of the present invention can be either hard-wired sensors or remote sensors. For example, in the embodiment illustrated in FIGS. 4A and 4B, the sensor includes a hard wire connector 20 to an analyzer and an input feed line 22 that can couple the energy fed to the device through the connector into the resonator 10 through the dielectric substrate 12. For example, the connector 20 can be a hard wire connection such as a coaxial cable connected to an analyzer.

Figure 7:
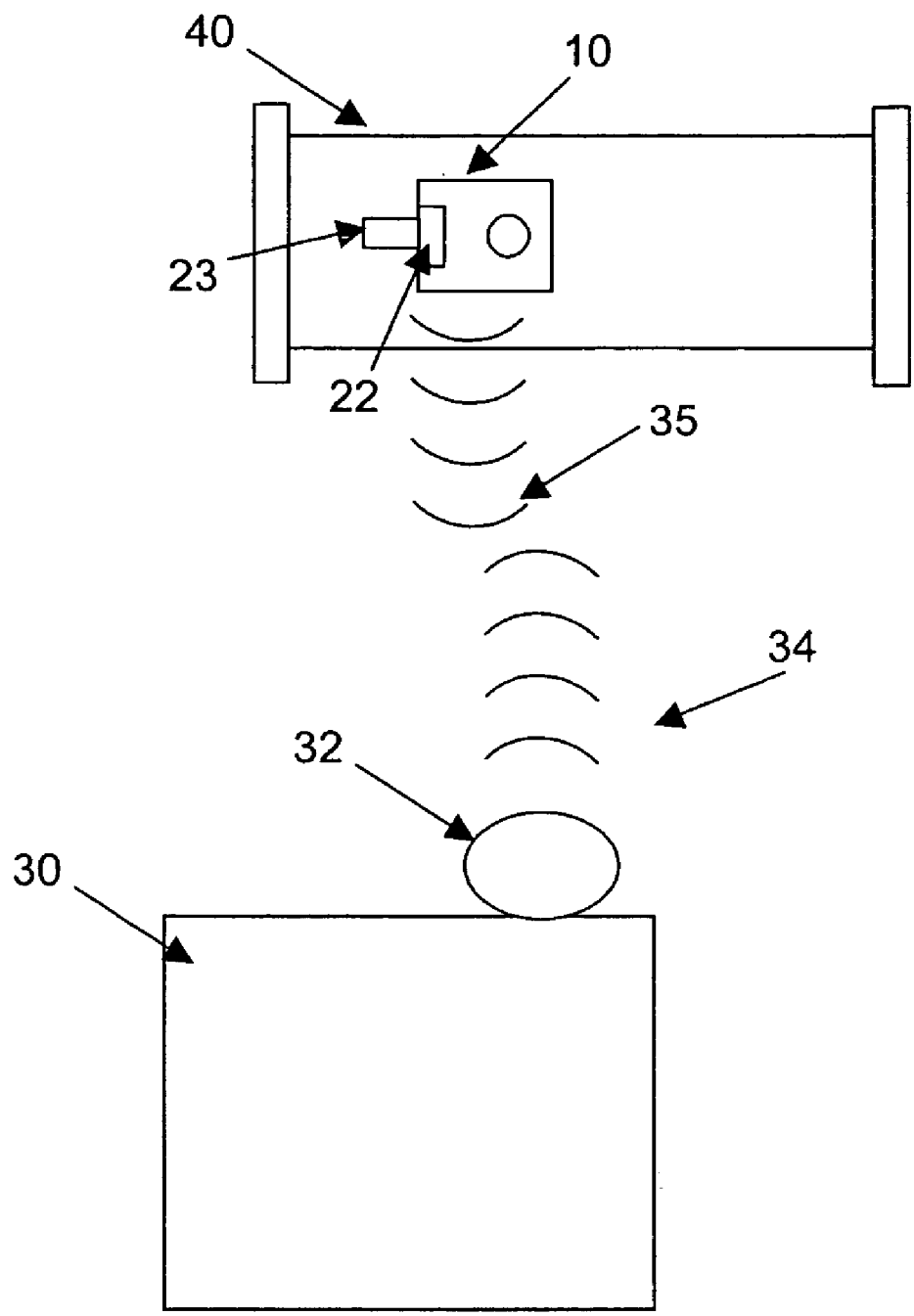
FIG. 7 is a schematic diagram of one embodiment of the disclosed sensors in a remote sensing application.

In another embodiment, illustrated in FIG. 7, the presently disclosed sensor can operate as a remote sensor. In this embodiment, the sensor can include an analyzer 30 that includes a transmitter/receiver antenna 32. During use, a microwave signal 34 transmitted from analyzer 30 can interact with the resonator via input receiver 23 coupled to input feed line 22 and monitor the resonant frequency of the resonator. Antenna 32 of the analyzer 30 can detect the return signal 35 at the resonant frequency of the resonator 10, and any resonant frequency shift upon adsorption of a material can be analyzed in a like manner to the hard wired system. Beneficially, in this embodiment, the sensor can be utilized in applications in which there may be intervening materials between the analyzer and the sensor. For example, in one embodiment, the enclosed chamber 40 can be an enclosed, air-tight packaging system, such as commonly used for food or medical products. In this embodiment, the sensor can detect the presence of gases or vapors within the packaging that could signal damaged goods.

Figure 5:
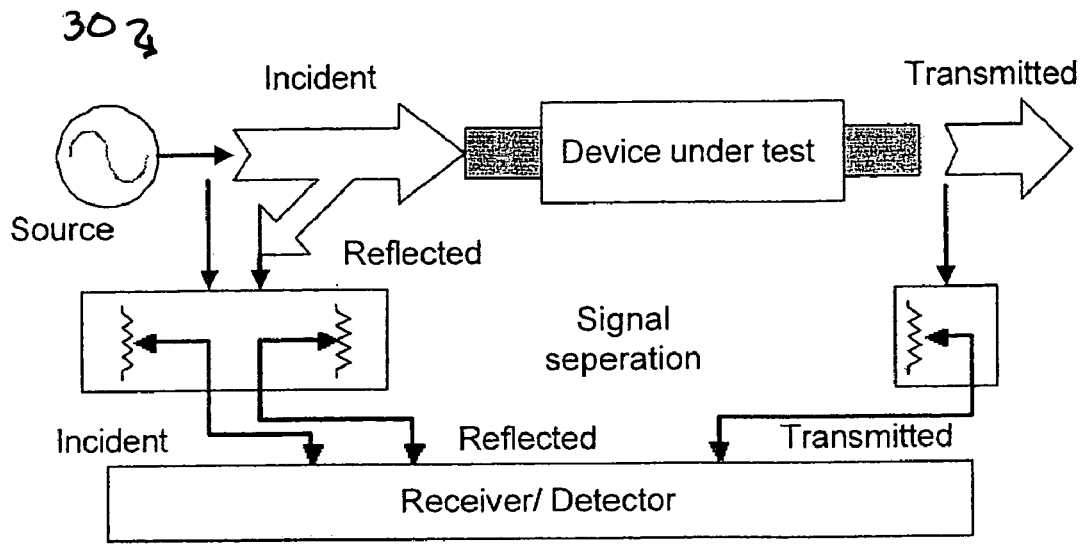
FIG. 5 is a block diagram of a network analyzer suitable for use with the resonant-circuit sensors of the present invention.

FIG. 5 illustrates a block diagram for one embodiment of a network analyzer generally 30 that can be used in conjunction with the resonator of the disclosed invention in either a hard wired or remote access configuration to obtain and manifest the resonant frequency of the resonator. In general, a suitable network analyzer 30 can include a sweeping signal source, a test set to separate forward and reverse signals, and a multi-channel, phase-coherent, highly sensitive receiver. As analysis methods and instrumentation necessary for the analyzer of the disclosed sensors is generally known in the art, a detailed description of such is not provided herein.

Utilizing suitable analysis methods and instrumentation, the resonant frequency shift of the resonator upon adsorption of a material to the carbon nanotubes contained in a layer of the resonator can be detected and analyzed and the adsorbed material can be identified based upon the measured shift in resonant frequency. In one embodiment of the present invention, the sensor can also detect and analyze the change in the Q-factor (loss in conductivity) of the resonator upon adsorption of a material in addition to the change in the resonant frequency. While not required by the disclosed sensors, the analysis of the Q-factor can serve as an additional variable to monitor the presence of adsorbed materials on the nanotube-containing layer of the resonator.

The resonant sensors of the disclosed invention can be used to detect a variety of different materials at very low concentrations. In particular, because the disclosed resonant sensors operate in the microwave regime, a very small change in the effective dielectric constant of the sensors, which can be generated in some embodiments by the presence of materials in as low as parts per billion concentrations, can lead to a discernable shift in the resonant frequency of the resonator. In addition, at low concentrations, and depending upon the nature of the detected material, the shift in resonant frequency can be proportional to the concentration of the detected material. As such, in certain embodiments, the disclosed sensors can also be utilized to analyze the concentration of a detected material.

As previously discussed, the effective dielectric constant of the resonator can vary depending upon the different materials in and on the resonator. Thus, when a material is adsorbed onto the carbon nanotubes, the effective dielectric constant of the resonator can shift and a corresponding shift in resonant frequency can be detected and analyzed. When the resonator of the sensor is formed and utilized as-prepared, that is, in air, this will naturally lead to a certain amount of material adsorbing to the nanotubes from the air. For example, oxygen, nitrogen and argon can be expected to adsorb to the nanotube layer of the sensor when the resonator is in air. This can shift the effective dielectric constant of the resonator. As such, the resonator of the present invention, when utilized as-prepared, under atmospheric conditions, may be 'blind' to certain materials, and particularly to certain non-polar and inert materials. In addition, the presence of materials previously adsorbed onto the nanotube layer can decrease the sensitivity of the resonator during sensing operations. As such, in one embodiment, the sensitivity and selectivity of the disclosed resonator sensors can be increased by degassing the nanotubes prior to use and utilizing the sensors with the resonator held in a degassed state.

Generally, the nanotubes held in the nanotube-containing layer can be degassed following formation of the resonator by holding the resonator at an elevated temperature for a period of time at low pressure. For example, in one embodiment, a resonator can be held at a pressure between about $1\times10^{-5}$ torr and about $2\times10^{-4}$ torr and simultaneously at a temperature of between about 100° C. and about 125° C. for at least about 12 hours to degas the nanotubes of the resonator. Following the degassing procedure, the resonator can be held at low pressure during cooling and utilization to prevent re-adsorption of atmospheric materials on the resonator.

Through the process of degassing the nanotubes, it has been found that not only can the sensors be utilized to detect materials to which they were previously 'blind' including non-polar and inert gases, for example, but in addition, the sensitivity of the sensors can be greatly increased. For example, when considering the detection of the polar gas ammonia, when utilizing a resonant sensor of the disclosed invention including a layer of SWNT as-prepared (that is, formed in air and not degassed following formation) the sensor can detect the presence of ammonia down to a concentration of about 100 ppm. In contrast, following a degassing procedure such as that outlined above, the disclosed sensors can detect the presence of ammonia down to a concentration of about 100 ppb.

In addition to the high sensitivity and selectivity of the disclosed sensors, the sensors of the present invention can also detect the presence of materials over a wide concentration span. For example, the disclosed sensors can detect the presence of polar gases, non-polar gases, and organic vapors in concentrations ranging from about 100 ppb to at least about 1500 ppm, or even higher in some embodiments, without saturating the sensor. This is believed to be primarily due to the high specific surface area of the nanotubes held in a layer of the resonator.

The sensors of the disclosed invention can have relatively fast response times to the presence of a material in a gaseous stream (i.e., a gas or vaporized material). For example, in certain embodiments, upon contact with a gaseous material, the disclosed sensors can exhibit a measurable change in resonant frequency within about ten minutes. In addition, the disclosed sensors can also exhibit a fast recovery time. For example, in those embodiments wherein as-prepared nanotubes are applied to the resonator and utilized for the detection of materials, such as polar gases like ammonia or organic vapors, the initial resonant frequency of the resonator can often be recovered within about ten minutes merely by evacuating the testing chamber of the gaseous material. When utilizing degassed nanotubes, the recovery period can be slightly longer, however, as the recovery of the initial resonant frequency of the resonator can often require a degassing process, in order to remove any molecules chemisorbed to the surface of the nanotube layer. Thus, in certain embodiments, complete recovery of the sensor can take somewhat longer, on the order of a few hours.

The disclosed invention can be better understood with references to the following examples.

EXAMPLE 1

Figure 6:
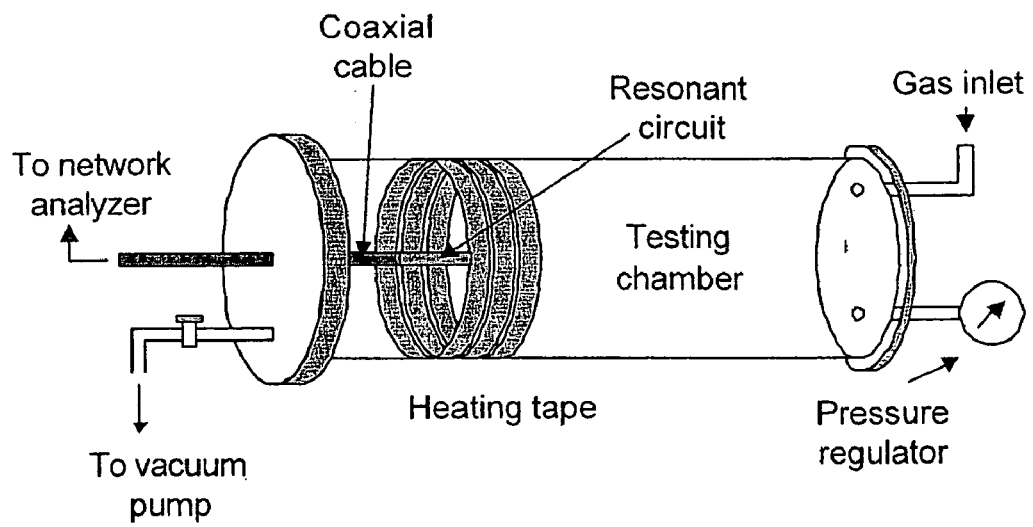
FIG. 6 is a schematic diagram of the testing apparatus used in the Examples.

A circular disk resonator such as that illustrated in FIGS. 4A and 4B was formed. The circular disk resonator included a Duroid Board (Rogers R04003) that was milled to fabricate a circular disk resonator resonating at 4 GHz. The surface of the micro-strip disk was coated to a depth of about 2 $\mu$m with a layer including single-walled nanotubes formed according to an arc-discharge process as illustrated in FIG. 1. The SWNT-containing layer was coated on the microstrip disk using a conductive epoxy (CW2400, Circuit Works) as the adhesive. This resonator sample was then placed in a testing chamber as illustrated in FIG. 6. The response of the sensor was monitored under different gas environments.

Figure 9:
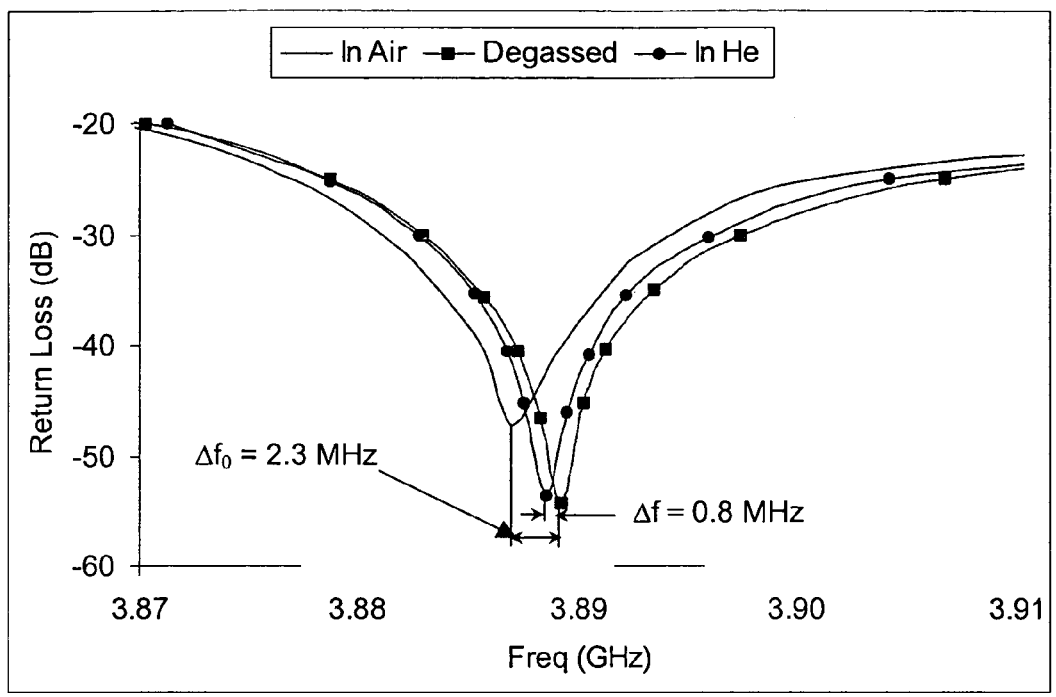

FIG. 9 shows the response of the resonator under helium. The solid line shows the response of the resonator in air. In air, the sensor displayed a resonant frequency of 3.887 GHz. The chamber was then pulled down to high vacuum (~$10^{-5}$ torr) and heated to ~125° C. for about 12 hours to degas the SWNTs. The testing chamber was then allowed to cool to room temperature. The second plot (squares) on FIG. 9 shows the sensor response after degassing. Following degassing, the resonator had a resonant frequency of 3.8893 GHz, having shifted from the previous value by 2.3 MHz ($\Delta f_0$). The resonator was then exposed to known amounts (~1500 ppm) of helium gas and the response of the sensor was measured after 10 minutes (circles). The resonant frequency shifted to 3.8885 GHz with a decrease of 0.8 MHz from the degassed value ($\Delta f$). Thus, inert gases were shown to interact with the nanotube-containing layer with a resulting change the dielectric constant of the system, changing the resonant frequency of the device. Another point that is evident from FIG. 9 is that in the process of degassing the nanotubes, the Q-factor increased, i.e., the conductivity increased.

EXAMPLE 2

Figure 10:
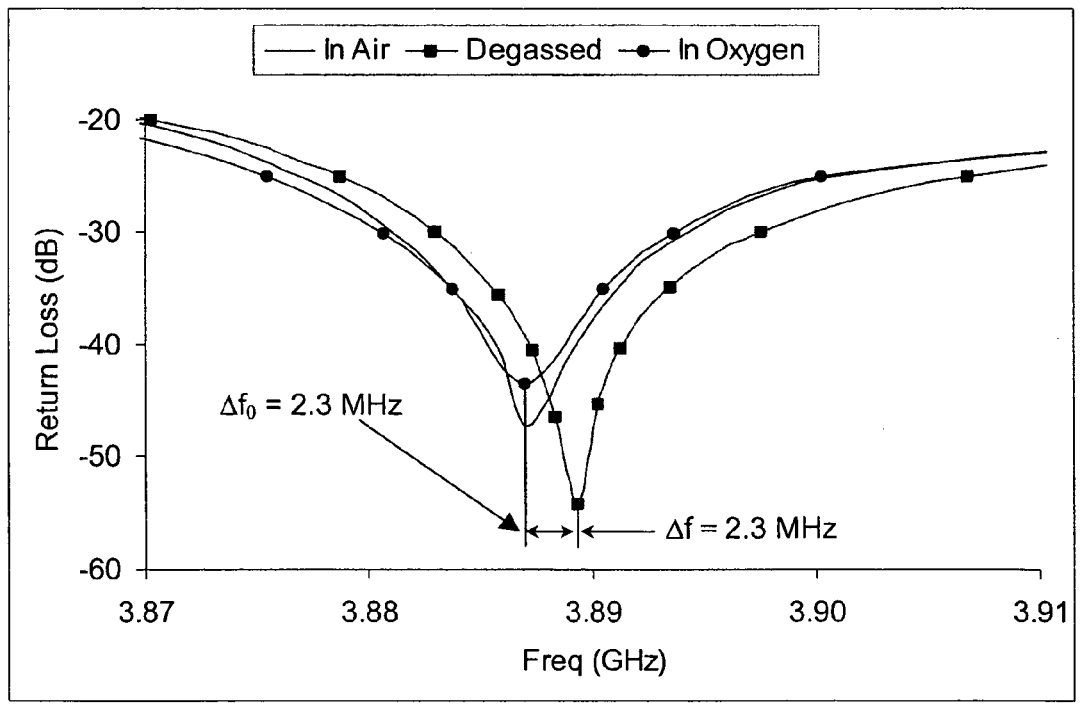

The response of the sensor of Example 1 was measured in oxygen. FIG. 10 shows the response of the resonator to oxygen. The first two curves are the same as the corresponding curves in FIG. 9. The third curve (circles) is the response of the sensor to oxygen. As can be seen, the resonant frequency of the resonator shifted from 3.8885 GHz in helium to 3.887 GHz in oxygen. This is very close to the resonant frequency value that was obtained in air. This strengthens the assumption that the electrical properties of pristine nanotubes are affected both by chemisorption and physisorption. This also reinforces the understanding that in as-prepared samples, the oxygen molecules have already interacted with the nanotubes and hence a similar shift was seen for air and oxygen gas exposures from the degassed value of resonant frequency.

Figure 11:
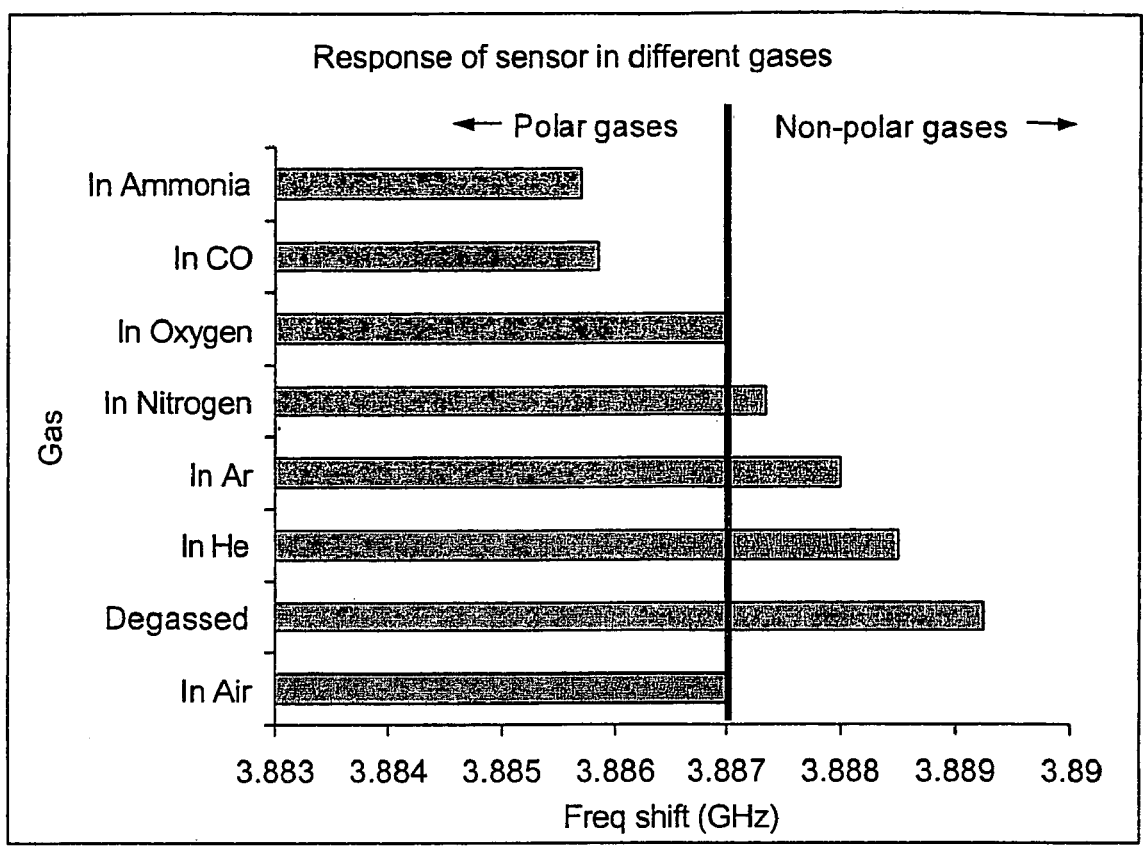

Measurements were also carried out with argon and nitrogen and proportional shifts in the resonant frequency of the sensor circuit were observed, as can be seen in FIG. 11. Thus, non-polar gases were shown to interact with pristine SWNTs and change their electrical properties. When as-prepared SWNT-containing sensors were exposed to these non-polar gases, no appreciable change in the resonant frequency of the sensor was detected.

EXAMPLE 3

Figure 8:
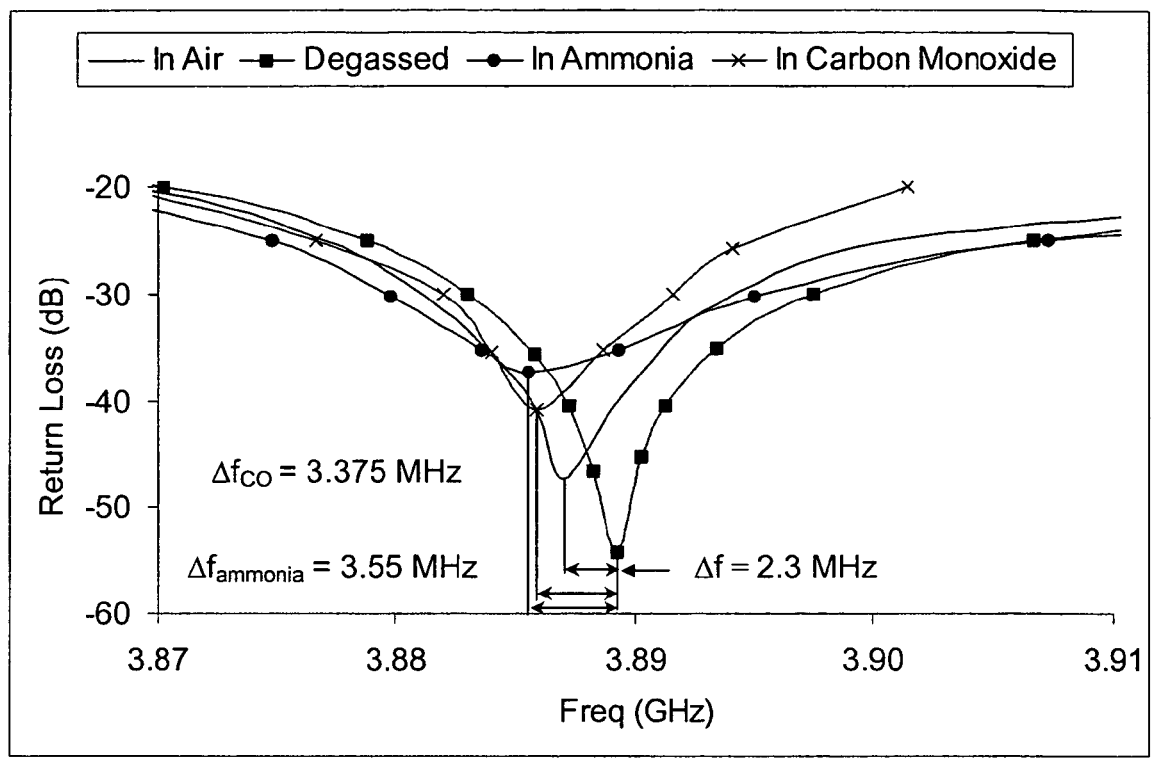
FIGS. 8–14 graphically illustrate the responses of resonant-circuit sensors of the present invention to various gases and organic solvent vapors.

Experiments were conducted on the degassed SWNT sensor circuits of Examples 1 and 2 to monitor their response to the presence of polar gases. FIG. 8 shows the response of a SWNT-containing sensor to ammonia and carbon monoxide. The first curve (solid line) is the response of the sensor in air with a resonant frequency of 3.887 GHz. The second curve (squares) is the response of the sample after the nanotubes have been degassed. These are the same as the corresponding curves as shown in FIGS. 9 and 10. The third curve (circles) is the response of the sensor circuit in carbon monoxide. The resonant frequency has shifted to 3.885875 GHz showing a downshift of 3.375 GHz. This shift is more than that of oxygen, which strengthens the belief that polar gases have a more pronounced effect on the dielectric properties of nanotubes. This can be due to the marked difference in the dielectric constants of polar and non-polar gases.

The fourth curve (crosses) shows the response of the SWNT sensor to ammonia. The resonant frequency shift in the case of ammonia exposure is slightly greater than that for carbon monoxide, which can be explained due to the relatively higher dielectric constant of ammonia with respect to CO, and also due to the larger amount of adsorption in the case of ammonia. The higher dielectric constant of ammonia is due to the higher dipole moment of the ammonia molecule and the larger amount of gas adsorption is believed to be due to the smaller molecular weight and higher adsorption energy of ammonia.

Another important fact that can be noticed in FIGS. 8–10 is the change in conductivity of the SWNT-containing sensor as it was exposed to different environmental conditions. As the as-prepared sample is degassed, the conductivity of the sensor increases, which is evident from the increase in the Q-factor of the sensor. Upon exposure of the sample to ammonia and carbon monoxide, the conductivity of the sensor decreases to a greater extent than when it was exposed to oxygen.

FIG. 11 summarizes the final resonant frequency of the resonator under the different environmental conditions of Example 1–3. The plot shows the measurements of the resonant frequency in air, vacuum, and in different gases used. The solid line clearly demarcates the resonant frequency of the resonator in the presence of polar and non-polar gases. Among the polar gases, ammonia shows a greater shift in the resonant frequency due to its higher dielectric constant (higher dipole moment) compared to carbon monoxide. For non-polar gases, the shift follows the heats of adsorption more closely than the molecular weight as is evident due to the higher shift of nitrogen when compared to helium. This is believed to be due to the fact that the dielectric constants of these gases vary as the inverse of the square root of the molecular weight and directly as the exponential power of the heat of adsorption. Thus, there is a stronger dependence of the resonant frequency shift on the heat of adsorption than molecular weight for non-polar gases.

EXAMPLE 4

Figure 12A:
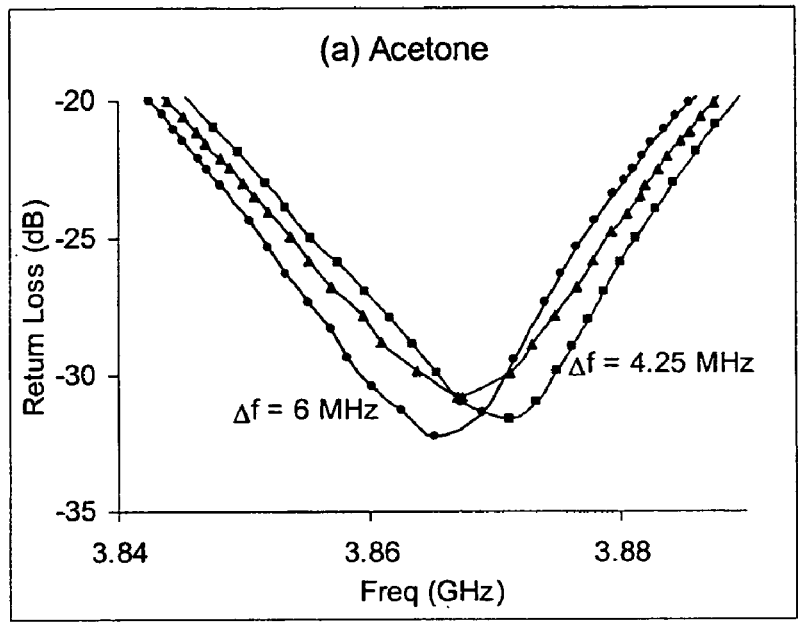
Figure 12B:
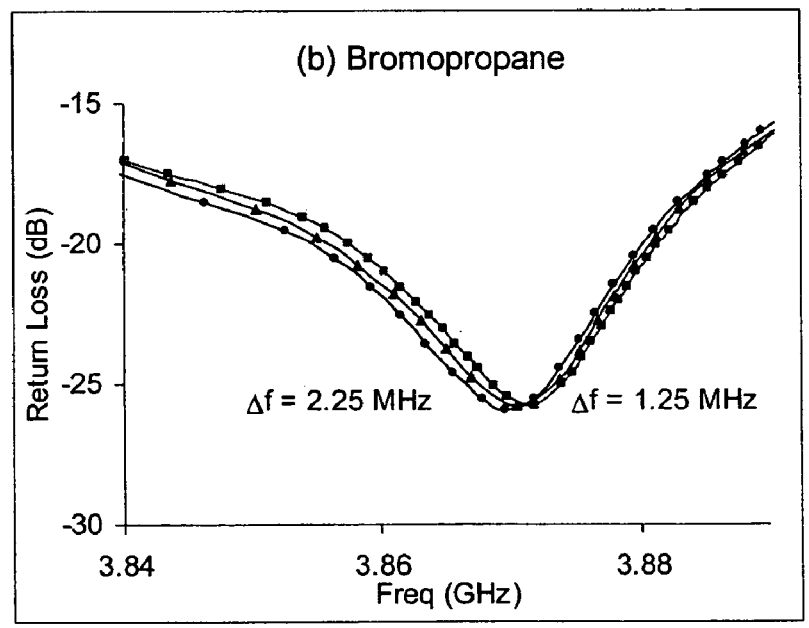

Electric-arc prepared SWNT bundles were physically coated on top of the conducting copper disk of a sensor as described in Examples 1–3. Electromagnetic energy was coupled into the resonator through a rectangular microstrip feed line. The SWNT layer was degassed by evacuating the testing chamber to $10^{-5}$ torr and simultaneously heating the chamber to ~130° C. for about 12 hours. The testing chamber was then cooled to room temperature while being maintained under high vacuum and the resonant frequency was recorded by a network analyzer before and after exposing the resonator to a known amount of gas or organic solvent vapor introduced into the chamber. The shift in resonant frequency was relatively large for vapors of acetone ($\epsilon_r=20$) compared to the corresponding shift for bromopropane ($\epsilon_r=8.1$) as seen by reference to FIG. 12A (illustrating the resonant frequency shift for acetone vapors) and 12B (illustrating the resonant frequency shift for bromopropane).

Figure 14:
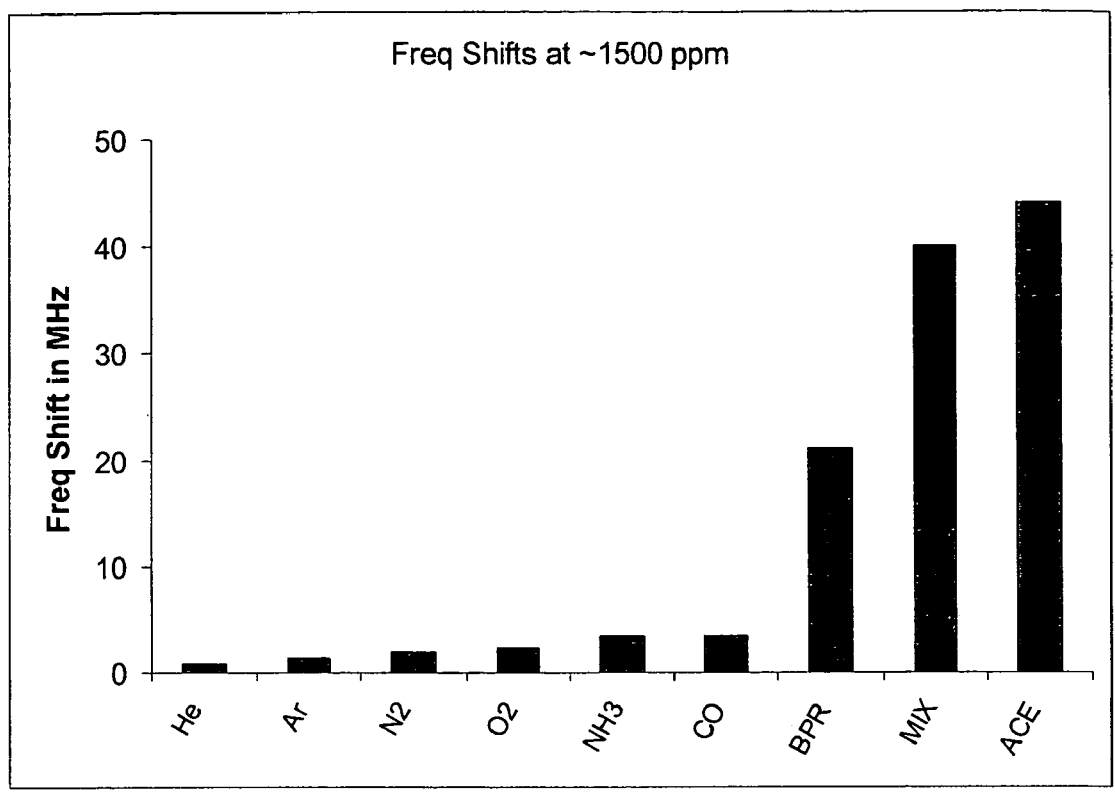

The shifts in the resonator frequency induced by the presence of ~1500 ppm of different gaseous materials (gases or organic liquids) are summarized in FIG. 14. These shifts ($\Delta f$) scale proportionally as a function of the dielectric ($\epsilon_r$) of the material, as indicated in the figures. All measurements were carried out under similar conditions using the same resonator for each of the materials shown in the Figure with a complete degassing cycle completed between exposures of the sensor to different materials. As can be seen, organic vapors with higher dielectric constants lead to a greater shift compared to the gases like nitrogen or oxygen, implying that the disclosed sensors can provide high selectivity for gas detection.

The change in resonant frequency for the resonator when exposed to a mixture of organic solvent vapors is also shown in FIG. 14. Again, the change in resonant frequency ($\Delta f$) for the mixture can be understood in terms of $\epsilon_r$ for each component in the gas mixture. For mixtures containing more than two components, a detailed modeling for $\Delta f$ in terms of $\epsilon_r$ could be obtained by routine experimentation to compare with the experimentally observed values of $\Delta f$.

EXAMPLE 5

Figure 13:
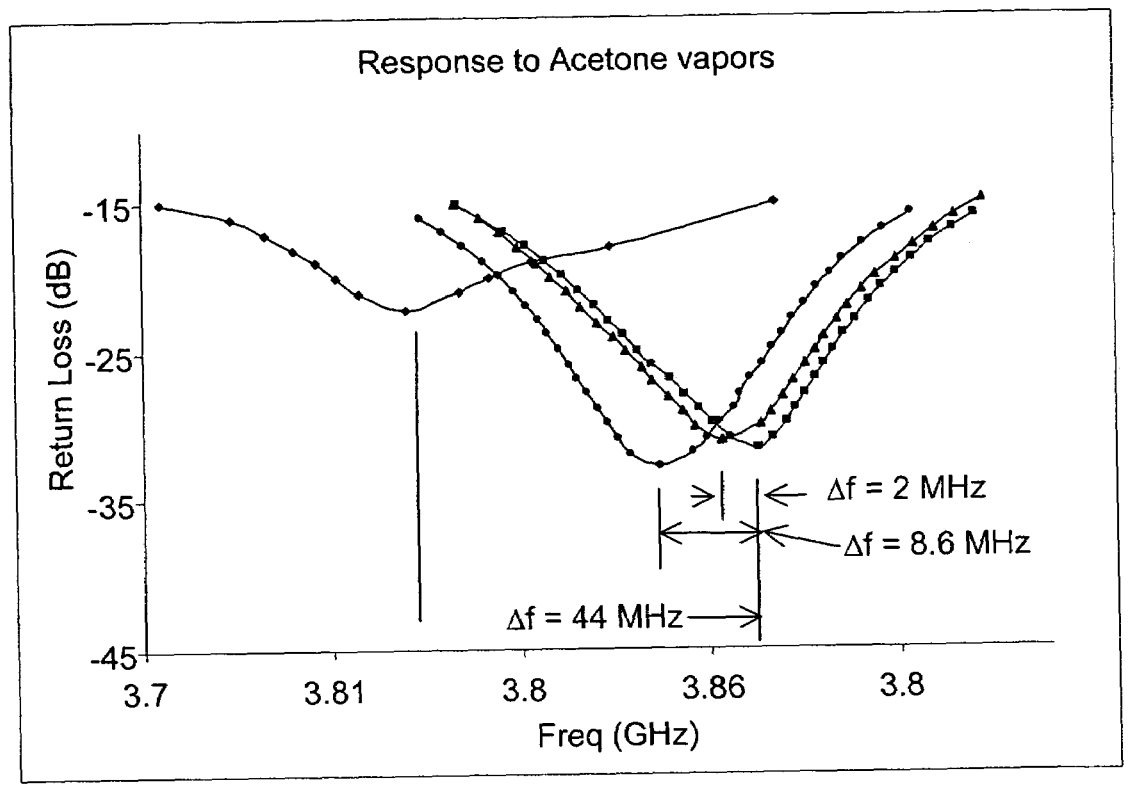

A resonant sensor including a layer containing degassed SWNT bundles such as that described for Example 4, above, was utilized to determine the response of the sensor to a gaseous flow including different concentrations of acetone vapors. The results are graphically illustrated in FIG. 13. The first curve (squares) is the response of the sensor in vacuum with a resonant frequency at about 3.87 GHz. The second curve (triangles) shows the response of the sensor to a gaseous flow containing acetone at a concentration of 800 ppb. As can be seen, at this concentration, the resonant frequency shifts from the vacuum resonant frequency by 2 MHz. The third curve (circles) corresponds to the response of the sensor to a gaseous flow containing acetone at a concentration of 15 ppm, and demonstrates a resonant frequency shift from the vacuum resonant frequency of 8.6 MHz. The fourth curve (squares) corresponds to the response of the sensor to a gaseous flow containing acetone at a concentration of 1300 ppm, and demonstrates a resonant frequency shift from the vacuum resonant frequency of 44 MHz. In addition to the change in resonant frequency, $\Delta f$, another evident feature in FIG. 13 is the decrease in the Q factor of the resonator upon exposure to different concentrations of acetone.

Similar to the unique resonant frequency of the sensors when in the presence of a known concentration of a given material, the change in resonant frequency of the sensors upon a change in concentration of a material will also be unique to that material. Thus, the disclosed sensors cannot only be utilized to identify a specific material in contact with the sensor, but, in certain embodiments, the disclosed sensors can also be utilized to determine the concentration of the material.

It will be appreciated that the foregoing examples, given for purposes of illustration, are not to be construed as limiting the scope of this invention. Although only a few exemplary embodiments of this invention have been described in detail above, those skilled in the art will readily appreciate that many modifications are possible in the exemplary embodiments without materially departing from the novel teachings and advantages of this invention. Accordingly, all such modifications are intended to be included within the scope of this invention which is defined in the following claims and all equivalents thereto. Further, it is recognized that many embodiments may be conceived that do not achieve all of the advantages of some embodiments, yet the absence of a particular advantage shall not be construed to necessarily mean that such an embodiment is outside the scope of the present invention.

What is claimed is:

1. A gas sensor comprising:
a resonator comprising a dielectric material, the resonator further including a layer comprising adsorptive nanostructures selected from the group consisting of degassed carbon nanotubes, activated carbon fibers, and adsorptive nanowires, wherein the dielectric material is in electrical communication with the layer comprising the adsorptive nanostructures such that the effective resonant frequency of the resonator depends upon the dielectric constant of the dielectric material and also depends upon the dielectric constant of the layer comprising the adsorptive nanostructures.

2. The gas sensor of claim 1 further comprising an analyzer in communication with the resonator for obtaining the resonant frequency of the resonator.

3. The gas sensor of claim 2, wherein the analyzer is in hard-wire communication with the resonator.

4. The gas sensor of claim 2, wherein the analyzer is in remote access communication with the resonator.

5. The gas sensor of claim 4, wherein the analyzer is in communication with the resonator via radio frequency signals.

6. The gas sensor of claim 1, wherein the resonator is a micro-strip circuit board resonator.

7. The gas sensor of claim 1, wherein the adsorptive nanostructures are degassed carbon nanotubes.

8. The gas sensor of claim 7, wherein the degassed carbon nanotubes comprise single-walled carbon nanotubes.

9. The gas sensor of claim 7, wherein the degassed carbon nanotubes comprise multi-walled carbon nanotubes.

10. The gas sensor of claim 1, wherein the layer comprising adsorptive nanostructures is about 2 $\mu$m in depth.

11. A gas sensor comprising:
a resonator comprising a dielectric material, the resonator further including a layer comprising adsorptive degassed carbon nanotubes, wherein the dielectric material is in electrical communication with the layer comprising the degassed carbon nanotubes such that the effective resonant frequency of the resonator depends upon the dielectric constant of the dielectric material and also depends upon the dielectric constant of the layer comprising the degassed carbon nanotubes, wherein the sensor indicates a measurable variation in resonant frequency of the resonator upon exposure to either polar or non-polar gases.

12. The gas sensor of claim 11 further comprising an analyzer in communication with the resonator for obtaining the resonant frequency of the resonator.

13. The gas sensor of claim 12, wherein the analyzer is in hard-wire communication with the resonator.

14. The gas sensor of claim 12, wherein the analyzer is in remote access communication with the resonator.

15. The gas sensor of claim 11, wherein the resonator is a micro-strip circuit board resonator.

16. The gas sensor of claim 11, wherein the degassed carbon nanotubes comprise single-walled carbon nanotubes.

17. The gas sensor of claim 11, wherein the degassed carbon nanotubes comprise multi-walled carbon nanotubes.

18. The gas sensor of claim 11, wherein the layer comprising degassed carbon nanotubes is about 2 $\mu$m in depth.

19. A gas sensor comprising:
a resonator comprising a dielectric material, the resonator further including a layer comprising adsorptive activated carbon nanofibers, wherein the dielectric material is in electrical communication with the layer comprising the activated carbon nanofibers such that the effective resonant frequency of the resonator depends upon the dielectric constant of the dielectric material and also depends upon the dielectric constant of the layer comprising the activated carbon nanofibers.

20. The gas sensor of claim 19 further comprising an analyzer in communication with the resonator for obtaining the resonant frequency of the resonator.

21. The gas sensor of claim 20, wherein the analyzer is in hard-wire communication with the resonator.

22. The gas sensor of claim 20, wherein the analyzer is in remote access communication with the resonator.

23. The gas sensor of claim 19, wherein the resonator is a micro-strip circuit board resonator.

24. The gas sensor of claim 19, wherein the layer comprising activated carbon nanofibers is about 2 $\mu$m in depth.

25. A gas sensor comprising:
a resonator comprising a dielectric material, the resonator further including a layer comprising adsorptive nanowires, wherein the dielectric material is in electrical communication with the layer comprising the adsorptive nanowires such that the effective resonant frequency of the resonator depends upon the dielectric constant of the dielectric material and also depends upon the dielectric constant of the layer comprising the adsorptive nanowires.

26. The gas sensor of claim 25 further comprising an analyzer in communication with the resonator for obtaining the resonant frequency of the resonator.

27. The gas sensor of claim 26, wherein the analyzer is in hard-wire communication with the resonator.

28. The gas sensor of claim 26, wherein the analyzer is in remote access communication with the resonator.

29. The gas sensor of claim 25, wherein the resonator is a micro-strip circuit board resonator.

30. The gas sensor of claim 25, wherein the layer comprising degassed carbon nanotubes is about 2 $\mu$m in depth.

* * * * *